US007183092B2

(12) United States Patent
Choi et al.

(10) Patent No.: US 7,183,092 B2
(45) Date of Patent: Feb. 27, 2007

(54) MODIFIED LUCIFERASE

(75) Inventors: Eileen H. Kim Choi, Flushing, NY (US); David R. Shonnard, Chassell, MI (US); Irina V. Rybina, Edgewater, NJ (US)

(73) Assignee: Board of Control of Michigan Technological University, Houghton, MI (US)

( * ) Notice: Subject to any disclaimer, the term of this patent is extended or adjusted under 35 U.S.C. 154(b) by 215 days.

(21) Appl. No.: 10/954,840

(22) Filed: Sep. 30, 2004

(65) Prior Publication Data

US 2005/0079567 A1 Apr. 14, 2005

Related U.S. Application Data

(60) Provisional application No. 60/508,458, filed on Oct. 3, 2003.

(51) Int. Cl.
*C12N 9/02* (2006.01)
*C12N 1/21* (2006.01)
*C12N 5/06* (2006.01)
*C12N 15/63* (2006.01)
*C07H 21/04* (2006.01)

(52) U.S. Cl. ................ 435/189; 435/252.3; 435/320.1; 435/325; 536/23.2

(58) Field of Classification Search ................ 435/189, 435/252.3, 320.1, 25
See application file for complete search history.

(56) References Cited

U.S. PATENT DOCUMENTS

| | | | |
|---|---|---|---|
| 5,219,737 A | 6/1993 | Kajiyama et al. |
| 5,229,285 A | 7/1993 | Kajiyama et al. |
| 5,650,289 A | 7/1997 | Wood |
| 5,670,356 A | 9/1997 | Sherf et al. |
| 6,265,177 B1 | 7/2001 | Squirrell et al. |

OTHER PUBLICATIONS

Andreotti, et al. (1994) Bioluminescence and Chemiluminescence: Fundamentals and Applied Aspects, Proceedings of the International Symposium on Bioluminescence and Chemiluminescence, 8th, Cambridge, UK, Sep. 5-8, 1994, pp. 403-406. Editor(s): Campbell et al., Publisher: Wiley, Chichester, UK.*
Kim-Choi et al (2006) Luminescence, vol. 21, No. 3, pp. 135-142.*
Kim-Choi et al (2006) Toxicology in Vitro, vol. 20, pp. 1537-1547.*
Andreotti et al., "Sensitivity Testing of Human Tumors Using a Microplate ATP Assay," *Bioluminescence and Chemiluminescence*, (Campbell, Kricka, Stanley eds.) pp. 403-406.
Branchini et al., "Identification of a Firefly Luciferase Active Site Peptide Using a Benzophenone-based Photooxidation Reagent," *J. Biological Chemistry*, (1997) 272-31:19359-19364.
Branchini et al., "Site-Directed Mutagenesis of Histidine 245 in Firefly Luciferase: A Proposed Model of the Active Site," *Biochemistry*, (1998) 37:15311-15319.
Branchini et al., "Site-Directed Mutagenesis of Firefly Luciferase Active Site Amino Acids: A Proposed Model for Bioluminescence Color," *Biochemistry*, (1999) 38:13223-13230.
Branchini et al., "The Role of Active Site Residue Arginine 218 in Firefly Luciferase Bioluminescence," *Biochemistry*, (2001) 40:2410-2418.
Conti et al., "Crystal Structure of Firefly Luciferase Throws Light on a Superfamily of Adenylate-Forming Enzymes," *Structure*, (1996) 4:287-298.
DeLuca et al., "Purification and Properties of Firefly Luciferase," *Methods in Enzymology*, (1978) 57:3-15.
DeWet et al., "Cloning of Firefly Luciferase cDNA and the Expression of Active Luciferase in *Escherichia coli*," *Proc. Natl. Acad. Sci.*, (1985) 82:7870-7873.
DeWet et al., "Firefly Luciferase Gene: Structure and Expression in Mammalian Cells," *Molecular and Cellular Biology*, (1987) 7:2:725-737.
Kajiuama et al., "Isolation and Characterization of Mutants of Firefly Luciferase Which Produce Different Colors of Light," *Protein Engineering*, (1991) 4:6:691-693.
Kajiyama et al., "Thermostabilization of Firefly Luciferase by a Single Amino Acid Substitution," *Biochemistry*, (1993) 32:13795-13799.
Kim et al., "Creating Mutant Luciferase Resistant to HPV Chemical Inhibition by Random Mutagenesis and Colony Level Screening," Abstract.
Kim et al., "Characterization of Chloroform Resistant Mutant Luciferase, CNBluc03-06," Abstract.
Kricka L.J., "Chemiluminescence and Bioluminescence," *Analytical Chemistry*, (1995) 67:12:499R-502R.
Lundin A., "Use of Firefly Luciferase in ATP-Related Assays of Biomass, Enzymes, and Metabolites," *Methods in Enzymologyl*, (2000) 305:346-370.
Price et al., "Luciferase and Recombinant Luciferase Labels," *J. Clinical Ligand Assay*, (1998) 21:4:349-357.
Seliger et al., "Spectral Emission and Quantum Yield of Firefly Bioluminescence," *Archives of Biochemistry and BiophysicsI*, (1960) 33:136-141.
Simpson et al., "The Effect of Detergents of Firefly Luciferase Reactions," *J. Bioluminescence and Chemiluminescence*, (1991) 6:97-106.
Tisi et al., "Development of a Thermostable Firefly Luciferase," *Analytica Chimica Acta*, (2002) 457:115-123.
Thompson et al., "Mutation of a Protease-sensitive Region in Firefly Luciferase Alters Light Emission Properties," *J. Biological Chemistry*, (1997) 272:30:18766-18771.
Wakuri et al., "Cytotoxicity Study of 32 Meic Chemicals by Colony Formation and ATP Assays," *Toxic. In Vitro*, (1993) 7:4:517-521.
White et al., "Improved Thermostability of the North American Firefly Luciferase: Saturation Mutagenesis at Position 354," *Biochem J.*, (1996) 319:343-350.

(Continued)

*Primary Examiner*—Elizabeth Slobodyansky
(74) *Attorney, Agent, or Firm*—Jeffrey D. Peterson; Michael Best & Friedrich LLP

(57) ABSTRACT

The invention comprises modified luciferase proteins which are more resistant to inhibition by test chemicals than wild type luciferase. The modified luciferases also contain greater thermostability than wild type luciferase.

15 Claims, 9 Drawing Sheets

OTHER PUBLICATIONS

Wood et al., "Introduction of Beetle Luciferases and their Applications," *J. Bioluminescence and Chemiluminescence*, (1989) 4:289-301.

Gould et al., "Firefly Luciferase as a Tool in Molecular and Cell Biology," *Analytical Biochemistry*, (1988)175:5-13.

Lundin, Arne, "Applications of Firefly Luminescence," *Bioluminescence and Chemiluminescence*, (1981) 187-197.

Baldwin, T.O., "Firefly luciferase: the structure is known, but the mystery remains," Structure (1996) 4:223-228.

* cited by examiner

SEQUENCE LISTING

```
<160> NUMBER OF SEQ ID NOS: 6

<210> SEQ ID NO 1
<211> LENGTH: 1650
<212> TYPE: DNA
<213> ORGANISM: Photinus pyralis

<400> SEQUENCE: 1
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
```

```
gcagttgcgc cgcgaacga catttataat gaacgtgaat tgctcaacag tatgaacatt      360
tcgcagccta ccgtagtgtt tgtttccaaa aagggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggatttaa tgaatacgat     540
tttgtaccag agtcctttga tcgtgacaaa acaattgcac tgataatgaa ttcctctgga     600
tctactgggt tacctaaggg tgtggccctt ccgcatagaa ctgcctgcgt cagattctcg     660
catgccagag atcctatttt tggcaatcaa atcattccgg atactgcgat tttaactgtt     720
gttccattcc atcacggttt tggaatgttt actacactcg atatttgat atgtggtttt     780 cgagtcgtct taatgtatag atttgaagaa gagctgtttt tacgatccct tcaggattac     840
aaaattcaaa gtgcgttgct agtaccaacc ctatttcat tcttcgccaa agcactctg     900 attgacaaat acgatttatc taatttacac gaaattgctt ctgggggcgc acctctttcg     960
aaagaagtcg gcgaagcggt tgcaaaacgc ttccatcttc cagggatacg acaaggatat     1020
gggctcactg agactacatc agctattctg attacacccg aggggatga taaaccgggc     1080 gcggtcggta agttgttcc atttttgaa gcgaaggttg tggatctgga tactgggaaa     1140
acgctgggcg ttaatcagag aggcgaatta tgtgtcagag acctatgat tatgtccggt     1200 tatgtaaaca atccggaagc gaccaacgcc ttgattgaca aggatggatg gctacattct     1260
ggagacatag cttactggga cgaagacgaa cacttcttca tagttgaccg cttgaagtct     1320
ttaattaaat acaaaggata tcaggtggcc cccgctgaat tggaatcgat attgttacaa     1380
caccccaaca tcttcgacgc gggcgtggca ggtcttcccg acgatgacgc cggtgaactt     1440
cccgccgccg ttgttgtttt ggagcacgga aagacgatga cggaaaaaga gatcgtggat     1500
tacgtcgcca gtcaagtaac aaccgcgaaa aagttgcgcg gaggagttgt gtttgtggac     1560
gaagtaccga aggtcttac cggaaaactc gacacaagaa aaatcagaga gatcctcata     1620
aaggccaaga agggcggaaa gtccaaattg                                       1650
```

<210> SEQ ID NO 2
<211> LENGTH: 550
<212> TYPE: PRT
<213> ORGANISM: Photinus pyralis

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
```

-continued

```
            130                 135                 140
Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Thr Val
225                 230                 235                 240

Val Pro Phe His His Gly Phe Gly Met Phe Thr Thr Leu Gly Tyr Leu
                245                 250                 255

Ile Cys Gly Phe Ala Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
                290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Phe
                500                 505                 510

Arg Gly Gly Val Val Phe Val Asp Glu Val Pro Lys Gly Leu Thr Gly
                515                 520                 525

Lys Leu Asp Thr Arg Lys Ile Arg Glu Ile Leu Ile Lys Ala Lys Lys
530                 535                 540

Gly Gly Lys Ser Lys Leu
545                 550
```

<210> SEQ ID NO 3
<211> LENGTH: 1650
<212> TYPE: DNA
<213> ORGANISM: Photinus pyralis

<400> SEQUENCE: 3

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg cgcgttatt tatcggagtt      300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggatttaa tgaatacgat     540
tttgtaccag agtcctttga cgtgacaaa acaattgcac tgataatgaa ttcctctgga     600
tctactgggt tacctaaggg tgtggccctt ccgcatagaa ctgcctgcgt cagattctcg     660
catgccagag atcctatttt tggcaatcaa atcattccgg atactgcgat tttaactgtt     720
gttccattcc atcacggttt tggaatgttt actacactcg atatttgat atgtggtttt     780
cgagtcgtct taatgtatag atttgaagaa gagctgtttt tacgatccct tcaggattac     840
aaaattcaaa gtgcgttgct agtaccaacc ctatttttcat tcttcgccaa agcactctg     900
attgacaaat acgattatc taatttacac gaaattgctt ctgggggcgc acctctttcg     960
aaagaagtcg gcgaagcggt tgcaaaacgc ttccatcttc cagggatacg acaaggatat    1020
gggctcactg agactacatc agctattctg attacacccg aggggatta taaaccgggc    1080
gcggtcggta agttgttcc atttttgaa gcgaaggttg tggatctgga tactgggaaa     1140
acgctgggcg ttaatcagag aggcgaatta tgtgtcagag acctatgat tatgtccggt    1200
tatgtaaaca atccggaagc gaccaacgcc ttgattgaca aggatggatg ctacattct     1260
ggagacatag cttactggga cgaagacgaa cacttcttca tagttgaccg cttgaagtct    1320
ttaattaaat acaaaggata tcaggtggcc cccgctgaat ggaatcgat attgttacaa    1380
caccccaaca tcttcgacgc gggcgtgca ggtcttcccg acgatgacgc cggtgaactt     1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacacaagaa aaatcagaga gatcctcata    1620
aaggccaaga agggcggaaa gtccaaattg                                     1650
```

<210> SEQ ID NO 4
<211> LENGTH: 550
<212> TYPE: PRT
<213> ORGANISM: Photinus pyralis

<400> SEQUENCE: 4

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30
```

-continued

Tyr Ala Leu Val Pro Gly Thr Ile Ala Phe Thr Asp Ala His Ile Glu
          35                  40                  45
Val Asn Ile Thr Tyr Ala Glu Tyr Phe Glu Met Ser Val Arg Leu Ala
 50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                  85                  90                  95
Phe Ile Gly Val Ala Val Ala Pro Ala Asn Asp Ile Tyr Asn Glu Arg
                 100                 105                 110
Glu Leu Leu Asn Ser Met Asn Ile Ser Gln Pro Thr Val Val Phe Val
             115                 120                 125
Ser Lys Lys Gly Leu Gln Lys Ile Leu Asn Val Gln Lys Lys Leu Pro
 130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                 165                 170                 175
Asn Glu Tyr Asp Phe Val Pro Glu Ser Phe Asp Arg Asp Lys Thr Ile
             180                 185                 190
Ala Leu Ile Met Asn Ser Ser Gly Ser Thr Gly Leu Pro Lys Gly Val
             195                 200                 205
Ala Leu Pro His Arg Thr Ala Cys Val Arg Phe Ser His Ala Arg Asp
         210                 215                 220
Pro Ile Phe Gly Asn Gln Ile Ile Pro Asp Thr Ala Ile Leu Thr Val
225                 230                 235                 240
Val Pro Phe His His Gly Phe Gly Met Phe Thr Thr Leu Gly Tyr Leu
                 245                 250                 255
Ile Cys Gly Phe Ala Val Val Leu Met Tyr Arg Phe Glu Glu Glu Leu
             260                 265                 270
Phe Leu Arg Ser Leu Gln Asp Tyr Lys Ile Gln Ser Ala Leu Leu Val
         275                 280                 285
Pro Thr Leu Phe Ser Phe Phe Ala Lys Ser Thr Leu Ile Asp Lys Tyr
     290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                 325                 330                 335
Arg Gln Gly Tyr Gly Leu Thr Glu Thr Thr Ser Ala Ile Leu Ile Thr
             340                 345                 350
Pro Glu Gly Asp Tyr Lys Pro Gly Ala Val Gly Lys Val Val Pro Phe
         355                 360                 365
Phe Glu Ala Lys Val Val Asp Leu Asp Thr Gly Lys Thr Leu Gly Val
     370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                 405                 410                 415
Trp Leu His Ser Gly Asp Ile Ala Tyr Trp Asp Glu Asp Glu His Phe
             420                 425                 430
Phe Ile Val Asp Arg Leu Lys Ser Leu Ile Lys Tyr Lys Gly Tyr Gln
         435                 440                 445
Val Ala Pro Ala Glu Leu Glu Ser Ile Leu Leu Gln His Pro Asn Ile

|       |       |       |
|-------|-------|-------|
| 450   | 455   | 460   |

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
            485                 490                 495

Glu Ile Val Asp Tyr Val Ala Ser Gln Val Thr Thr Ala Lys Lys Phe
                500                 505                 510

Arg Gly Gly Val Val Phe Val Asp Glu Val Pro Lys Gly Leu Thr Gly
            515                 520                 525

Lys Leu Asp Thr Arg Lys Ile Arg Glu Ile Leu Ile Lys Ala Lys Lys
    530                 535                 540

Gly Gly Lys Ser Lys Leu
545                 550

<210> SEQ ID NO 5
<211> LENGTH: 1650
<212> TYPE: DNA
<213> ORGANISM: Photinus pyralis

<400> SEQUENCE: 5

| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggatttaa tgaatacgat | 540 |
| tttgtaccag agtcctttga tgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg gatatttgat atgtggtttt | 780 |
| cgagtcgtct taatgtatag atttgaagaa gagctgtttt tacgatccct tcaggattac | 840 |
| aaaattcaaa gtgcgttgct agtaccaacc ctatttttcat tcttcgccaa aagcactctg | 900 |
| attgacaaat acgatttatc taatttacac gaaattgctt ctgggggcgc acctctttcg | 960 |
| aaagaagtcg gcgaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc attttttgaa gcgaaggttg tggatctgga tactgggaaa | 1140 |
| acgctgggcg ttaatcagag aggcgaatta tgtgtcagag acctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga aagacgatga cggaaaaaga gatcgtggat | 1500 |
| tacgtcgcca gtcaagtaac aaccgcgaaa aagttgcgcg gaggagttgt gtttgtggac | 1560 |

```
gaagtaccga aaggtcttac cggaaaactc gacgcaagaa aaatcagaga gatcctcata      1620
aaggccaaga agggcggaaa gtccaaattg                                       1650
```

<210> SEQ ID NO 6
<211> LENGTH: 550
<212> TYPE: PRT
<213> ORGANISM: Photinus pyralis

<400> SEQUENCE: 6

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Ala Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350
```

-continued

```
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
        370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
        450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Phe
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
        530                 535                 540
Gly Gly Lys Ser Lys Leu
545             550
```

MODIFIED LUCIFERASE

CROSS-REFERENCE TO RELATED APPLICATIONS

This application claims the benefit of U.S. Provisional Application No. 60/508,458, filed Oct. 3, 2003, which is incorporated herein by reference.

FIELD OF THE INVENTION

Toxicity testing of industrial chemicals is becoming an increasing priority for many chemical manufacturers. However, obtaining toxicity data using whole animal models is expensive, time consuming, and increasingly being perceived as cruel and unethical. Numerous institutions and researchers have been working towards developing and validating reliable and robust in vitro methods for evaluating acute toxicity. Although it may not be feasible to completely replace whole animal studies with in vitro methods, progress has been significant and several in vitro methods are close to being validated internationally.

Viable cells maintain a strictly regulated concentration of internal ATP. The cytotoxicity of chemicals can be assessed by measuring the ATP concentrations in treated and untreated cells. Luciferase is a very sensitive and accurate measure of ATP concentration in cells. Luciferase catalyzes the oxidation of its substrate, D-luciferin, in the presence of ATP, $Mg^{2+}$ and molecular oxygen, emitting light with a quantum yield of 0.88.

The reaction scheme is as follows:

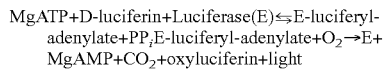

The bioluminescence reaction catalyzed by luciferase covers a wide range of applications. Luciferase is actively used in the detection of microorganisms, in genetic reporter assays, and cytotoxicity measurements during drug discovery.

Despite many applications, wild type firefly luciferase of *Photinus pyralis* has shown limitations due to its instability. One of the limitations of luciferase is inhibition of the enzyme reaction by chemicals commonly used in an ATP assay. This inhibition has contributed to limited applications of luciferase for high production volume (HPV) chemical testing. Chloroform ($CHCl_3$) is one HPV chemical that inhibits wild type luciferase activity significantly.

Previously, several research teams have successfully used random mutagenesis and screening to isolate mutants of luciferase from different species of fireflies. Kajiyama and Nakano showed that single amino acid replacements on luciferase from Japanese fireflies, *Luciola Cruciata* and *Luciola Laterali* can have an effect on thermostability or on the wavelength of the light emitted. [N. Kajiyama and E. Nakano (1991) *Prot. Eng.* 4, 691–693 and N. Kajiyama and E. Nakano (1993) *Biochemistry* 32, 13795–13799, both references incorporated herein by reference.] Peter White and David Squirrell also used random mutagenesis to create a thermostable mutant luciferase. [P. J. White, D. J. Squirrell, P. Arnaud, C. R. Lowe, and A. H. Murray (1996) *Biochem. J.* 319, 343–350, incorporated herein by reference.]

The present invention is directed towards mutating the polynucleotide sequence which codes for luciferase to create a modified luciferase resistant to inhibition by the test chemicals and testing toxicity of HPV chemicals.

SUMMARY OF THE INVENTION

The invention comprises modified luciferase proteins which are more resistant to inhibition by test chemicals than wild type luciferase. The modified luciferases also contain greater thermostability than wild type luciferase. The modified luciferases also exhibit high activity at elevated pH (up to pH 11) under conditions which completely inhibit wild type luciferase. These improved enzyme characteristics can lead to a wider range of applications for in-vitro cytotoxicity screening in drug discovery and devleopment and toxicity testing of high production volume chemicals. The modified luciferases are more active than wild type luciferase in the absence of the stabilizing agent DTT (dithiothreitol) and may have benefits in applications where passport proteins are used in gene reporter assays.

In one aspect of the invention, a modified luciferase is provided in which the amino acid sequence of the luciferase differs from wild type luciferase in that serine is replaced by threonine at amino acid 239. In another aspect of the invention a modified luciferase is provided in which the amino acid sequence of the luciferase differs from wild type luciferase in that alanine is replaced by threonine at amino acid number 532.

In yet another aspect of the invention a modified luciferase is provided in which the amino acid sequence of the luciferase differs from wild type luciferase in that serine is replaced by threonine at amino acid 239, and alanine is replaced by threonine at amino acid number 532. In still another aspect of the invention a modified luciferase is provided in which the amino acid sequence of the luciferase differs from wild type luciferase in that serine is replaced by threonine at amino acid 239, aspartic acid is replaced by tyrosine at amino acid 357 and alanine is replaced by threonine at amino acid number 532.

The invention also comprises a fusion protein which contains the modified luciferase.

The present invention also comprises polynucleotides which encode the modified luciferases, and vectors containing these polynucleotides. Host cells transformed by the vectors are also contemplated by the invention.

The invention also contemplates a method of selecting a modified luciferase polypeptide which exhibits greater activity in the presence of a chemical than wild type luciferase. The method comprises obtaining a polynucleotide which encodes wild type luciferase. Random mutagenesis is performed on the wild type polynucleotide to create a library of multiple modified luciferase polypeptides. The activity of each of the multiple modified luciferase polypeptides is tested in the presence of a chemical. A modified luciferase polypeptide which exhibits greater activity in the presence of the chemical than wild type luciferase is selected. Suitably such chemicals include chloroform, ethanol, methylene chloride, toluene, hexane, xylene, heptane and hexane.

Other advantages and a fuller appreciation of specific adaptations, compositional variations, and physical attributes will be gained upon an examination of the following detailed description of preferred embodiments, taken in conjunction with the appended claims.

Figure 1:
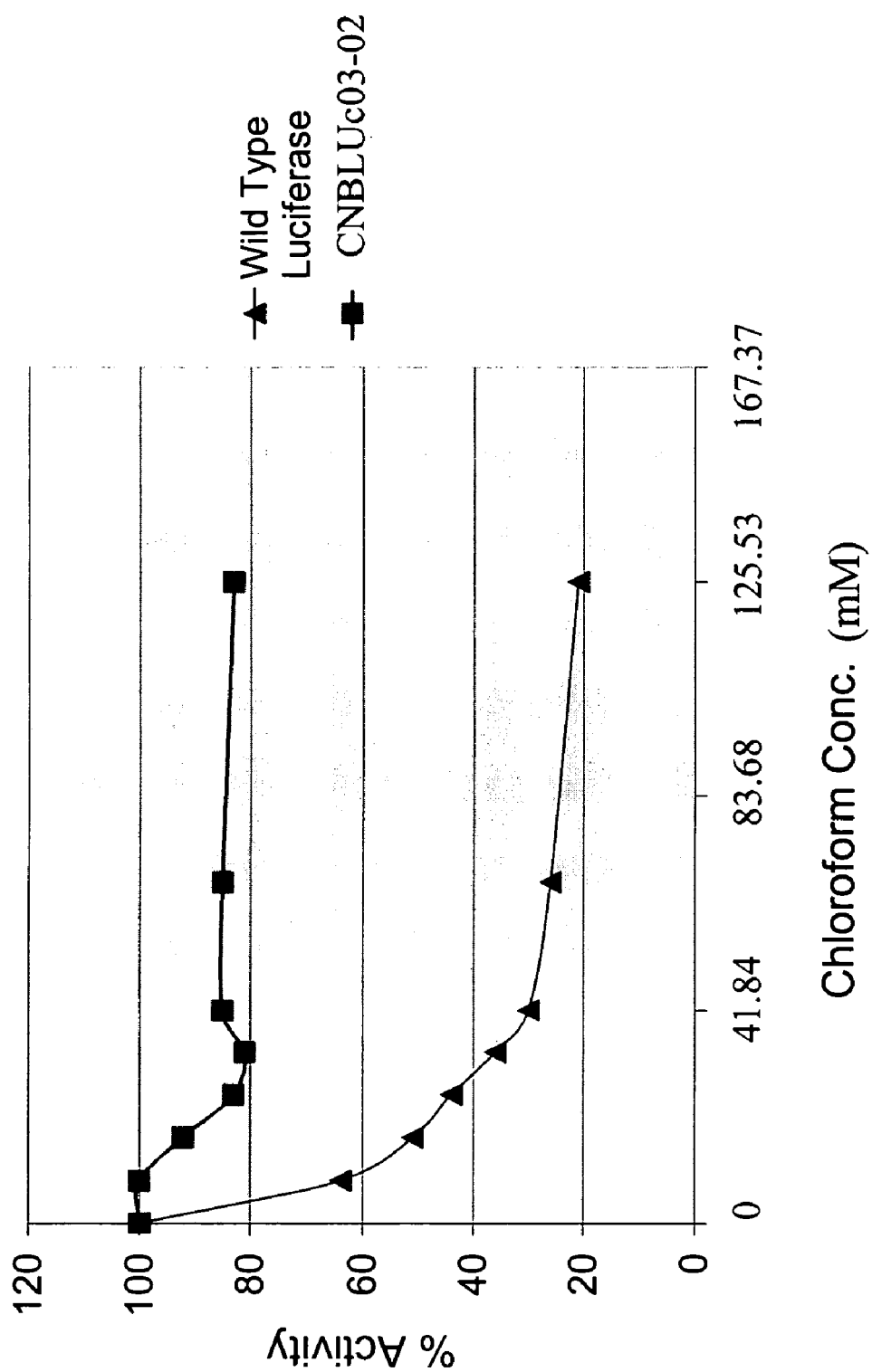
FIG. 1 is a plot showing the effect of increasing concentration of chloroform on wild type luciferase and CNBLuc03-02 luciferase (SEQ ID NO: 2) activity.

Before the embodiments of the invention are explained in detail, it is to be understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION OF THE INVENTION

The invention comprises modified luciferase proteins which are more resistant to inhibition by test chemicals than wild type luciferase. Such test chemicals include HPV chemicals. HPV chemicals include chloroform, toluene, ethanol, dichloromethane, hexane, 1,4 dimethylbenzene, heptane, methylene chloride, sodium dodecyl sulfate, 1,2-dichloroethane, chloroethene, ethylbenzene, styrene, cyclohexane, (1-methylethyl)-benzene, nonene, 1,2 dimethylbenzene, 1,1,1-trichloroethane, diethylbenzene, 1,1-dichloroethane, 3,4-dichloro-1-butene, chlorobenzene, 1,1,2-trichloroethane, 1-octene, 1-decene, naphthalene and chloroethane.

The modified luciferases also contain greater thermostability than wild type luciferase. The modified luciferases also exhibit high activity at elevated pH (up to pH 11) under conditions which completely inhibit wild type luciferase. The modified luciferases are also more active than wild type luciferase in the absence of the stabilizing agent DTT (dithiothreitol).

The term "wild type" luciferase refers to the amino acid sequence of luciferase of the species *Photinus pyralis* (SEQ ID NO: 6). One polynucleotide which codes for the wild type luciferase is SEQ ID NO: 5.

In one aspect of the invention a modified luciferase SEQ ID NO: 2 is provided in which the amino acid sequence of the luciferase differs from wild type luciferase in that serine is replaced by threonine at amino acid 239, and alanine is replaced by threonine at amino acid number 532. In another aspect, the invention provides a modified luciferase of SEQ ID NO: 4. The luciferase of SEQ ID NO. 4 differs from wild type luciferase (SEQ ID NO: 6) in that serine is replaced by threonine at amino acid 239, aspartic acid replaced by tyrosine at amino acid 357 and alanine is replaced by threonine at amino acid number 532.

In a further embodiment the modified luciferases (SEQ ID NO: 2 and SEQ ID NO: 4) may be in the form of fusion proteins or incorporate polypeptide extensions. This may improve the ease by which they can be produced, localized in vivo or extracted and purified.

In another aspect of the invention the invention comprises a polynucleotide which encodes the modified luciferase SEQ ID NO: 2. Suitably this polynucleotide sequence comprises SEQ ID NO: 1. The invention also comprises a polynucleotide which encodes the modified luciferase SEQ ID NO: 4. Suitably this polynucleotide sequence comprises SEQ ID NO: 3.

The invention also comprises a polynucleotide sequence which contains a region which encodes either the modified luciferase SEQ ID NO: 2 or the modified luciferase of SEQ ID NO: 4.

The invention also comprises vectors comprising a polynucleotide which encodes, or has a region which encodes, for either the modified luciferase SEQ ID NO: 2 or the modified luciferase of SEQ ID NO: 4. The vectors can include a replication element which permits replication of the vector in a suitable host cell and/or a promoter element which permits expression of said polynucleotide in a suitable host cell. In another aspect of the invention, the invention comprises a host cell containing, or transformed with, a vector of the invention.

The present invention is further explained by the following examples which should not be construed by way of limiting the scope of the present invention.

EXAMPLE 1

Creation of Mutated Luciferases

A. Creation of Template

Gateway Technology PCR Cloning System from Invitrogen was used to subclone the Luc gene from pGEM-Luc (Promega) (gene for luciferase of *Photinus pyralis* into a Histidine-tag vector, pDEST17. The nucleotide sequence of the luc gene is SEQ ID NO: 5. The polypeptide sequence of the product of the luc gene is SEQ ID NO: 6. Gateway Technology uses the bacteriophage lambda site-specific recombination system. This system facilitates the integration of lambda into the *E-coli* chromosome and the switch between the lytic and lysogenic pathways (Invitrogen Gateway). Gateway Technology is composed of two recombination reactions: the BP reaction for creating the entry clone (DONR201+Luc) and the LR reaction to generate the destination clone (pDEST17+Luc). After the BP reaction, the luc gene has L attachment sites for the LR reaction. However once the LR reaction is performed the luc gene gains back B attachment sites.

PCR fragment luc gene with B attachments was first subcloned into pDOR201 by the BP recombination reaction. The entry vector then was transformed into competent *E-Coli*, DH5α cells (invitrogen), plated on LB agar+30 μg/ml kanamycin plates and grown overnight. The purified plasmid from DH5α cells containing entry vector was used in second recombination reaction, LR reaction. LR reaction product was then transformed into competent *E-Coli*, DH5α cells and plated on LB agar+100 μg/ml ampicillin plates for overnight growth. The destination vector (pDEST17+luc) had an ampicillin resistant gene to avoid contamination by the entry vector.

B. First Generation Random Mutagenesis—Creation of CNBLuc03-02

The GeneMorph™ PCR Mutagenesis Kit from Stratagene was used for random mutagenesis of luciferase. The plasmid pDONR201 containing the Luc gene was used as a template for error-prone PCR amplification. The oligonucleotide primers designed to produce PCR fragments with attachment L sites were used in order to proceed to LR recombination reaction directly after PCR.

The mutagenized plasmid (pDEST17+mutant Luc) was initially transformed into competent E. coli DH5α cells (invitrogen). The entire mutant luciferase library was preserved by purifying plasmids from scraped cells of all transformation plates using Qiagen MiniPrep plasmid purification kit.

(i) Qualitative Screening of Colonies

1 μl of purified plasmid (~80 ng/μl) containing mutant luciferase was used for transformation into competent E. coli, BL21 (DE3) cells for better expression level. 40 plates (LB agar with 100 μg/ml ampicillin) containing approximately 150 colonies per plate were generated from each transformation. Plates were sealed and stored at 4° C. for at least two days before screening.

For primary screening, cells from each transformation plate were first transferred onto nitrocellulose membranes. Nitrocellulose membranes containing transferred colonies were placed on filter paper soaked with screening solution consisting of 0.5 mM D-luciferin, 10% (vol.) Ethanol, 5% (vol.) Chloroform and 40 mM Tris-Acetate buffer, pH 5.5, colonies facing up, in a Petri-dish. The low pH condition is to aid in the transport of D-luciferin across the cell wall during screening. Ethanol is present as a co-solvent to solubilize chloroform. Co-solvents are often used for in vitro assays, for either ATP detection or other assays using different endpoints. After incubating the membrane the bioluminescence was detected with X-ray film using Kodak X-omat processor model 1000A, exposure time being not more than 30 seconds. The colonies emitting the brightest light were selected for secondary screening. Approximately 400 colonies out of 6000 were selected from primary screening.

For secondary screening, selected colonies were grown overnight in 200 μl LB broth with 100 μg/ml ampicillin in 52 wells of a deep/clear 96-well plate overnight at 30° C. Two copies of bacterial cells grown in 96-well plates were generated using a sterilized metal pin replicator on LB agar+100 μg/ml ampicillin plates. Cells were grown at 30° C. overnight. One copy was used for secondary screening in the same manner as in primary screening, leaving the other copy for inoculation of selected mutants. After the secondary screening of 400 colonies, about 50 colonies were selected for final in vitro luciferase activity assay.

(ii) Quantitative In vitro Screening and Selection of Mutants

Selected colonies from secondary screening were inoculated and grown in 5 ml LB broth containing 100 μg/ml ampicillin at 30° C. overnight. When the $OD_{660}$ reached approximately 1, bacterial cells were harvested from 1.5 ml of culture by centrifugation for 3 min at 12,000 rpm (Eppendorf centrifuge model 5415D). Harvested cells were resuspended in 1 ml of 40 mM Tris-Acetate buffer, pH 7.8, and sonicated for 10 seconds using a Branson Sonifer 450, Duty cycle-40 and output control-4. The activity of each luciferase sample, prepared using 10 μl of supernatant from a subsequent centrifugation of sonicated bacterial cell culture, was tested in 200 μl total reaction volume by a Luminometer (Perkin Elmer, model Victor II). Each assay contained 40 mM Tris-Acetate, 1 mM $MgSO_4$, 0.1 mM EDTA (ethylenediaminetetraacetic acid), 33 mM DTT (dithiothreitol), 500 μM D-Luciferin, 10% Ethanol and 500 μM ATP at pH 7.8. Some screening assays also contained 68.8 mM chloroform (0.8% vol.).

Different mutant luciferases were compared quantitatively by determining the percentage (%) inhibition of luciferase activity in the presence of chloroform relative to a control without chloroform. The specific activities of chloroform-tolerant mutants were generally lower as compared to wild type. Of two isolated colonies with high tolerance to chloroform treatment, a mutant that had comparable activity and was inhibited much less by chloroform (CNBLuc03-02) was finally obtained. The nucleotide sequence of CNBLuc03-02 is SEQ ID No: 1. The polypeptide sequence of the product of SEQ ID No: 1 is SEQ ID No: 2.

C. Second Generation Random Mutagenesis—Creation of CNBLuc03-06.

The general protocol for second generation random mutagenesis, including transformation and screening protocols, was essentially the same as for the first generation of random mutagenesis, as described in Section B of this example, with an exception of the template. The intermediate mutant luciferase gene (CNBLuc03-02, SEQ ID NO: 1) from the first random mutagenesis was used as a template. The intermediate mutant in pDEST17 vector had B attachment sites resulting from a previous LR reaction. Two new adaptor primers designed for B attachment sites were used for error-prone PCR amplification.

The new library, PCR fragments with B attachment sites, was used for the BP recombination reaction. The entry clone, pDONR201, containing the second generation mutant luc genes, was transformed into competent E-Coli, DH5α cells. These cells were plated on LB agar+30 μg/ml kanamycin plates for overnight growth. Plasmids from all the scraped colonies were purified and used for the LR recombination reaction.

Finally, pDEST17, containing second generation mutant luc genes, was transformed into competent E-Coli, DH5α cells. After screening the library generated from second generation random mutagenesis, a mutant luciferase, CNBLuc03-06, was obtained that was not only resistant to, but also had the capacity to be activated by chloroform. The nucleotide sequence of CNBLuc03-06 is SEQ ID NO: 3. The polypeptide sequence of the product of SEQ ID NO: 3 is SEQ ID NO: 4.

EXAMPLE 2

Stability of CNBLuc03-02 Luciferase in the Presence of Potential Inhibitors

The stability of CNBLuc03-02 luciferase (SEQ ID NO: 2) in the presence of a range of potential inhibitors was assayed. The basic assay contained 40 mM Tris-Acetate at pH 7.8, 1 mM $MgSO_4$, 0.1 mM EDTA (ethylenediaminetetraacetic acid), 500 μM D-Luciferin and 500 μM ATP. Ethanol, DTT (dithiothreitol) and potential inhibitors were included at the concentrations stated.

A. Stability Of CNBLuc03-02 in the Presence of Chlorform

In the presence of 5% ethanol, 33 mM DTT and 0.8% chloroform, CNBLuc03-02 luciferase (SEQ ID NO: 2) from 10 μl cell lysates showed only about a 30% inhibition by 0.8% $CHCl_3$ whereas the wild type luciferase was inhibited over 80% in the same condition. FIG. 1 shows that 10 μl cell lysates containing CNBLuc03-02 luciferase (SEQ ID NO: 2) assayed at different concentrations of chloroform in the presence of 33 mM DTT and 5% ethanol were found to maintain 80% of the original activity, whereas wild-type luciferase was reduced to about 20% of the original activity under the same conditions.

Figure 2:
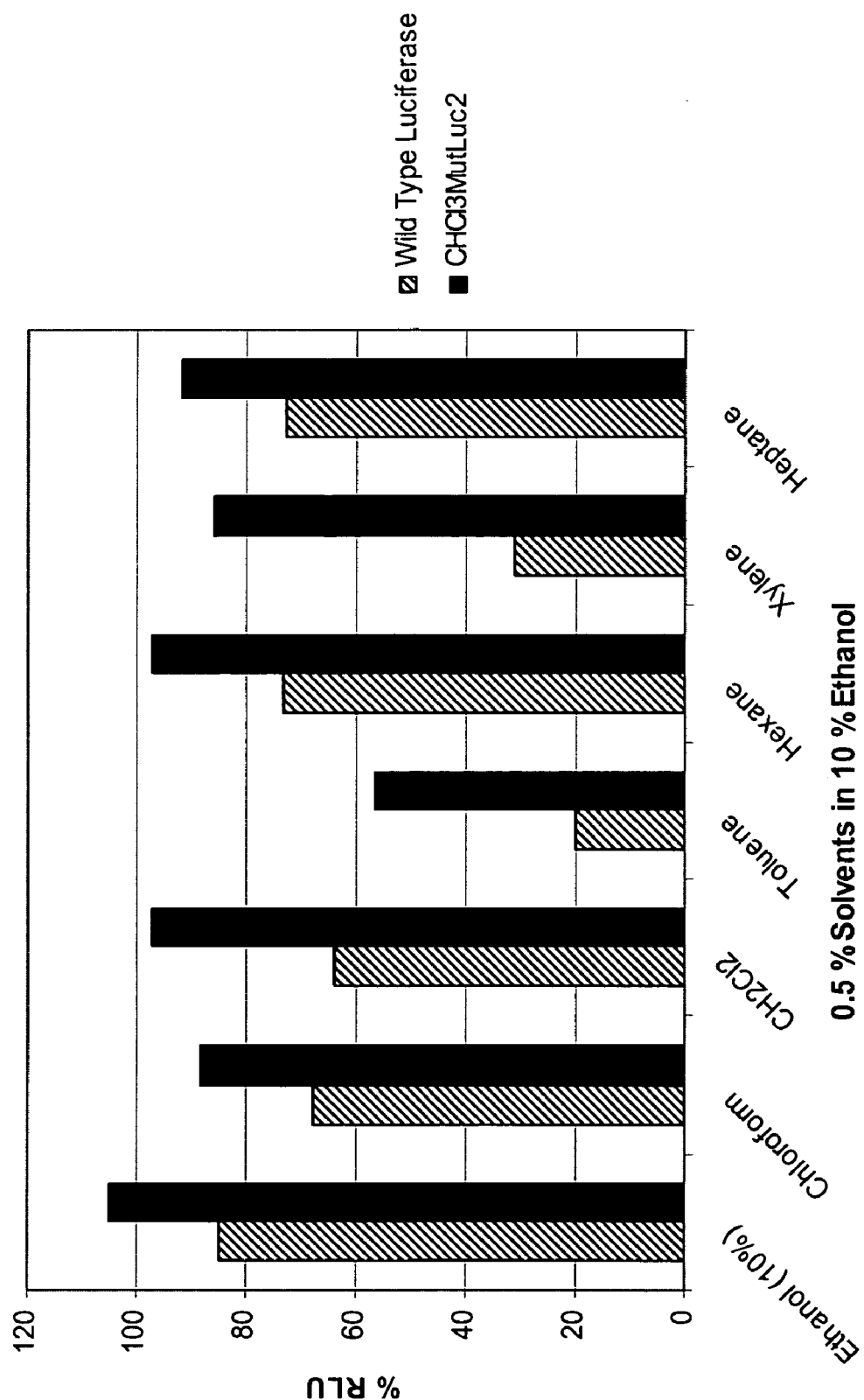
FIG. 2 is a plot showing the stability of CNBLuc03-02 luciferase (SEQ ID NO: 2) over wild type luciferase in the presence of 10% Ethanol and 0.5% of various solvents.

B. Stability of CNBLuc03-02 Luciferase in the Presence of High Production Volume Chemicals Five different HPV solvents ($CH_2Cl_2$, toluene, hexane, xylene, and heptane), known to inhibit wild-type luciferase activity, were selected to demonstrate the stability of CNBLuc03-02 luciferase (SEQ ID NO: 2). FIG. 2 shows that in the presence of 0.5% of each selected solvent, 33 mM DTT and 10% ethanol, CNBLuc03-02 luciferase (SEQ ID NO: 2) activity from 10 μl cell lysate was not inhibited as much as wild-type luciferase from 10 μl cell lysate, and CNBLuc03-02 luciferase (SEQ ID NO: 2) activity was not inhibited more than 15%, except when tolulene was present. Toluene inhibited CNBLuc03-02 luciferase (SEQ ID NO: 2) activity by approximately 40% and wild type luciferase activity by approximately 80%.

EXAMPLE 3

Stability of CNBLuc03-06 Luciferase in the Presence of Potential Inhibitors

The stability of CNBLuc03-06 luciferase (SEQ ID NO: 4), both in purified form and in cell lysates, in the presence of a range of potential inhibitors was assayed. The basic assay contained 40 mM Tris-Acetate at pH 7.8, 1 mM $MgSO_4$, 0.1 mM EDTA (ethylenediaminetetraacetic acid), 500 μM D-Luciferin and 500 μM ATP. Ethanol, DTT (dithiothreitol) and potential inhibitors were included at the concentrations stated.

A. Purification of CNBLuc03-06 Luciferase

Purified CNBLuc03-06 luciferase (SEQ ID NO: 4) was made by first inoculating 1 L LB broth (100 μg/ml ampicillin) with *E. coli* BL21 (DE3) cells containing the pDEST17 vector with a His-tagged CNBLuc03-06 and growing the cells at 30° C. overnight. Cells were then induced by IPTG (40 μM) to promote luciferase production and cultured for 3 hours. The cells were harvested by centrifugation (on sorval model RC5C, rotor SLA-1500, 10 min 7,000 g, 0–4° C.). Harvested cells were resuspended in 50 ml 100 mM Tris-Acetate buffer, pH 7.8, and sonicated 3 times for 1 min (sonicated on Branson model sonifer 450, output control—6, duty cycle—constant, on ice). The soluble fraction obtained after centrifugation was used for ammonium sulfate fractionation.

Luciferase was precipitated in the range of 50–70% ammonium sulfate. The sample was further purified by affinity chromatography using a Nickel Chelating column (*Amersham Pharmacia*, HiTrap). Steps of 50 mM and 200 mM of Imidazole were used to wash the column of non-specific binding proteins. Luciferase was eluted using 500 mM imidazole, and imidazole was removed from the recovered enzyme using a desalting column (*Amersham Pharmacia*, HiPrep 26/10). The purified luciferase, CNBLuc03-06 (SEQ ID NO: 4), was analyzed by SDS PAGE Gel-Electrophoresis using a 4–12% precasted using Duramide gel (*Cambrex Rockland*) run at 150 Volts for approximately 40 minutes. The Coomassie stained gel showed no significant contaminants.

B. Stability of CNBLuc03-06 Luciferase in the Presence of High Production Volume Chemicals Using the basic assay and in the presence of 5% ethanol, 33 mM DTT and 0.8% chloroform, CNBLuc03-06 luciferase (SEQ ID NO: 4) from cell lysates was found to be activated by about 30% compared with the absence of chloroform. This effect was confirmed by repeated experiments. With 20 ng purified CNBLuc03-06 luciferase (SEQ ID NO: 4) and in the presence of of 2.5% ethanol, 1 mM DTT and 86 mM chloroform an activation of approximately 50% was measured, compared with the absence of chloroform.

Figure 3:
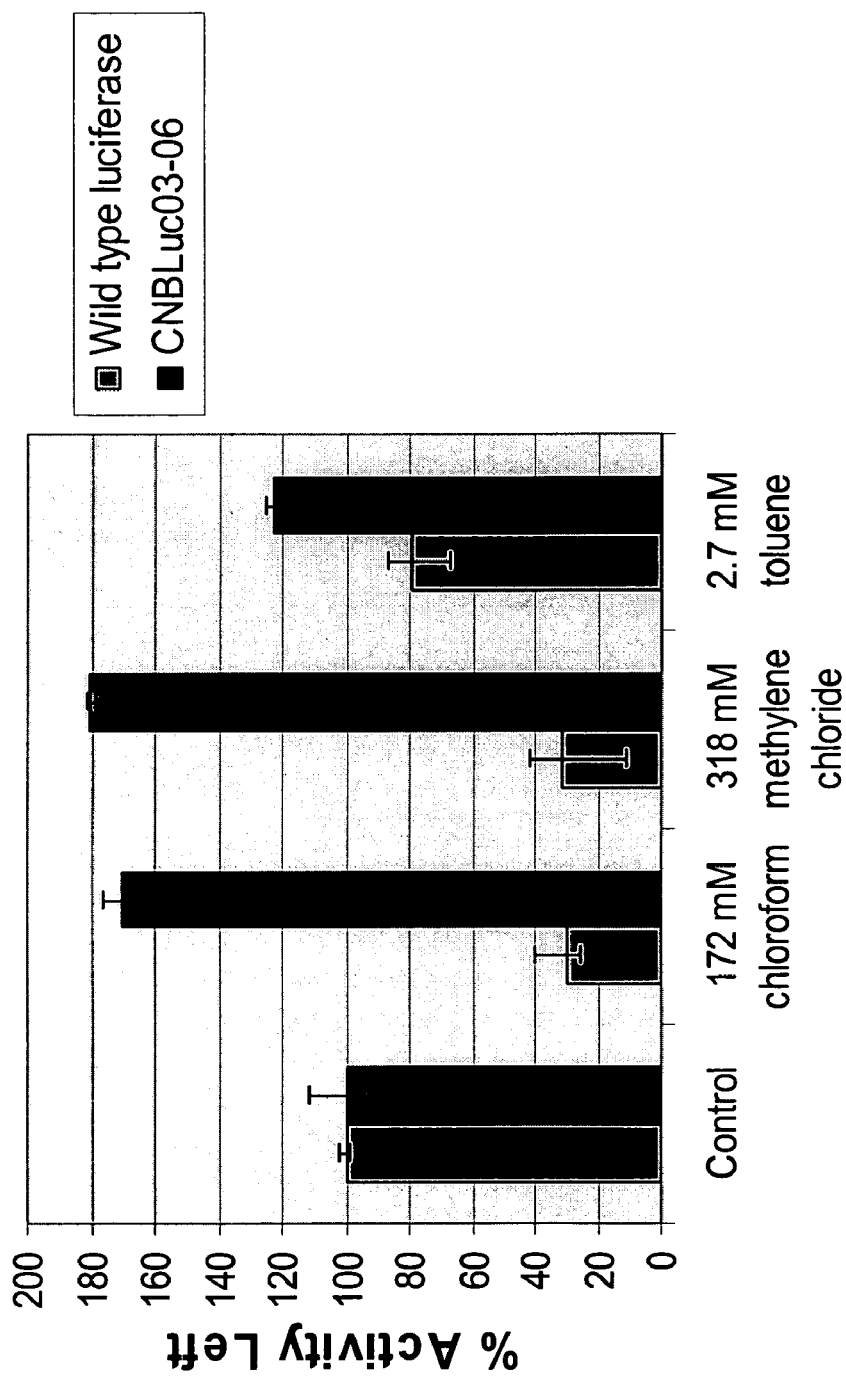
FIG. 3 is a plot showing the effect of higher concentration of chloroform, methylene chloride and toluene on wild type luciferase and CNBLuc03-06 luciferase (SEQ ID NO: 4) activity.

The capacity of a variety HPV chemicals to inhibit or activate both wild type luciferase and CNBLuc03-06 luciferase (SEQ ID NO: 4) activity compared to controls without HPV chemicals was tested. Higher concentrations of chloroform (172 mM), methylene chloride (318 mM) or toluene (2.7 mM) were used. The basic assay contained 20ng of purified CNBLuc03-06, 1 mM DTT and 2.5% ethanol. CNBLuc03-06 luciferase (SEQ ID NO: 4) was exposed to each chemical for less than 5 minutes before measuring the light output. FIG. 3 shows that wild-type was inhibited by about 70% compared to controls for both chloroform and methylene chloride and was inhibited by about 20% for tolulene, whereas CNBLuc03-06 luciferase (SEQ ID NO: 4) was activated by approximately 60% for chloroform, activated by approximately 80% for methylene chloride and activated by approximately 20% for tolulene.

C. Stability of CNBLuc03-06 in the Presence of Detergents

The stability of CNBLuc03-06 luciferase (SEQ ID NO: 4) in the presence of Triton X-100 and SDS was determined using 20 ng of purified luciferase per sample using the basic assay conditions and in the presence of 0% ethanol and 33 mM DTT. The effect of detergents on wild type luciferase was determined previously by W. J. Simpson and J. R. M. Hammond (W. J. Simpson and J. R. M. Hammond, (1991) *Journal of Bioluminescence & Chemiluminescence*, 6. 97–106, incorporated herein by reference). They reported the anionic detergents inhibit luciferase activity, and cationic detergents and nonionic detergents increase the reaction rate when the concentration of detergent exceeds critical micelle concentration (CMC) value but only up to certain concentrations. As expected both wild type luciferase and CNBLuc03-06 luciferase (SEQ ID NO: 4) were activated by the nonionic detergent, Triton X-100, up to final concentration of 1.25% in the reaction.

Figure 4:
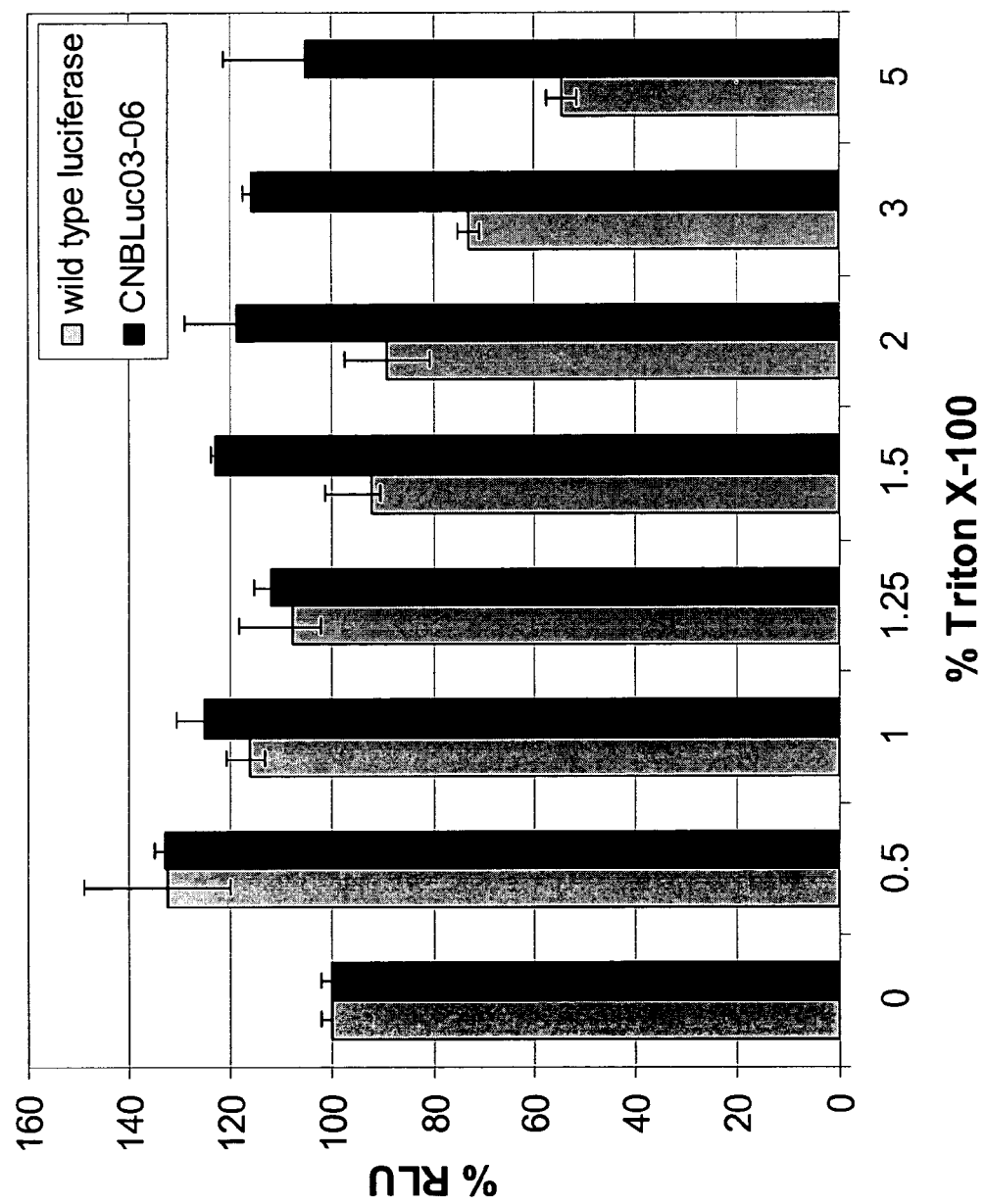
FIG. 4 is a plot comparing the activities of wild type luciferase and CNBLuc03-06 luciferase (SEQ ID NO: 4) in the presence of increasing concentration of non-ionic detergent, Triton X-100.

FIG. 4 shows that wild type luciferase activity increased until 1.25% then it started decreasing as Triton X-100 concentration increased up to 5%. For CNBLuc03-06 luciferase (SEQ ID NO: 4) activity showed a similar trend as wild type luciferase, but maintained activities above the control at all concentrations of Triton X-100.

Figure 5:
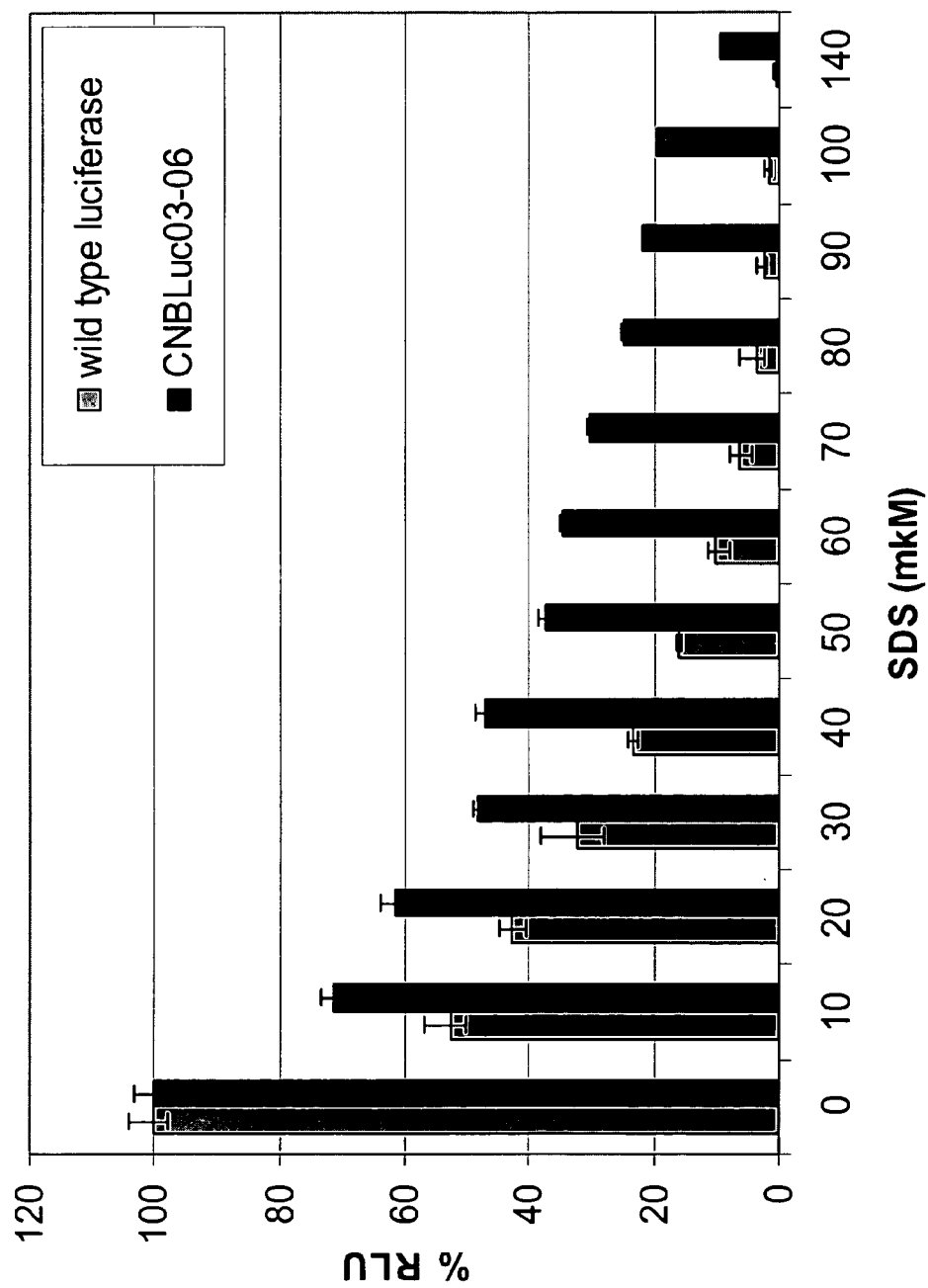
FIG. 5 is a plot showing the effect of an anionic detergent, SDS on wild type luciferase and CNBLuc03-06 luciferase (SEQ ID NO: 4) activities.

SDS was used for testing the effect of anionic detergents. FIG. 5 shows that even small concentrations of SDS inhibited luciferase activity significantly for both wild type luciferase and CNBLuc03-06 luciferase. However, CNBLuc03-06 luciferase (SEQ ID NO: 4) retained much more activity at all concentrations of SDS compared to wild type luciferase.

EXAMPLE 4

Thermostability of CNBLuc03-06 Luciferase

Figure 6:
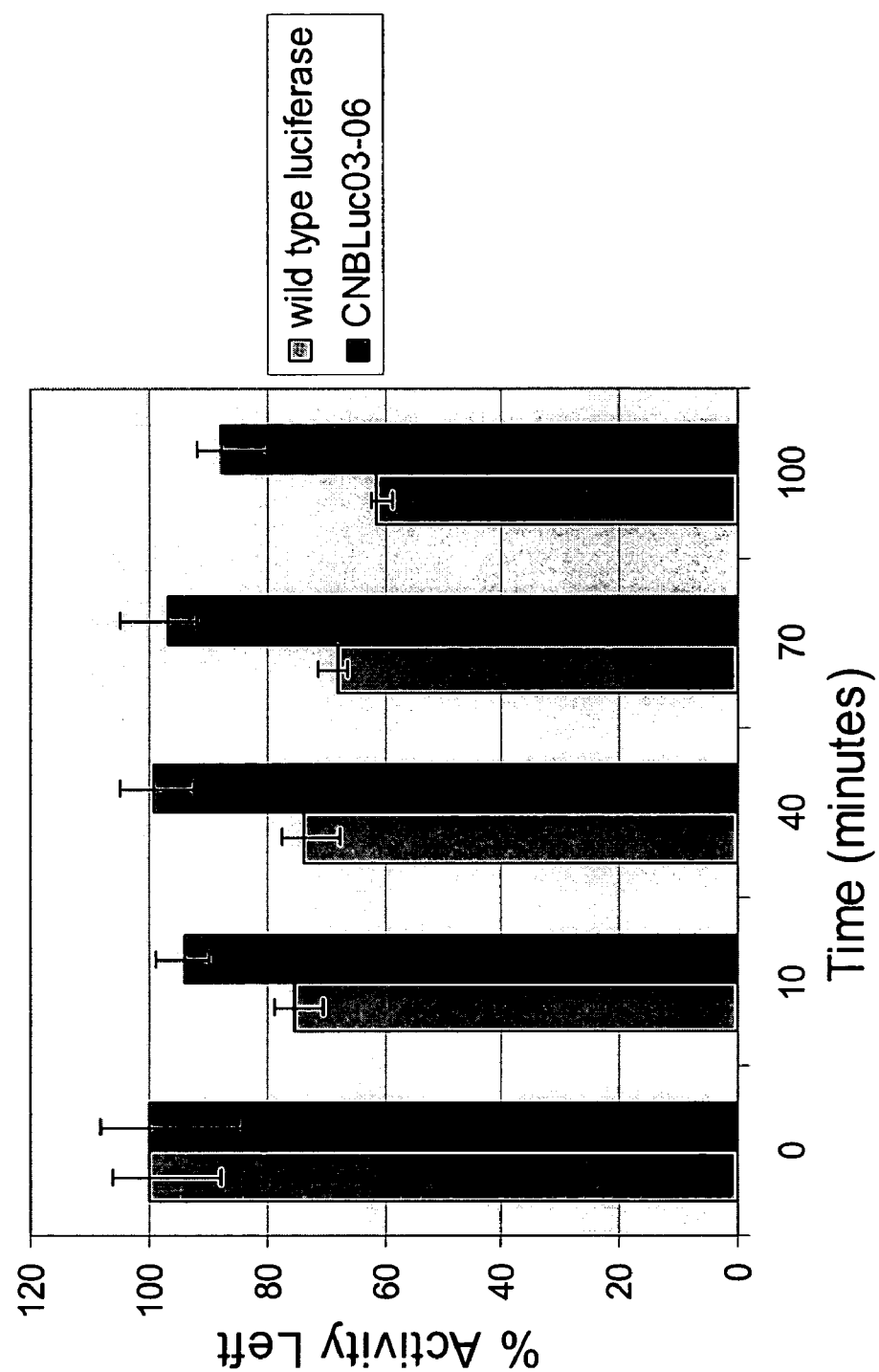
FIG. 6 is a plot comparing the activities of wild type luciferase and CNBLuc03-06 luciferase (SEQ ID NO: 4) kept at a temperature of 0° C. over time.
Figure 7:
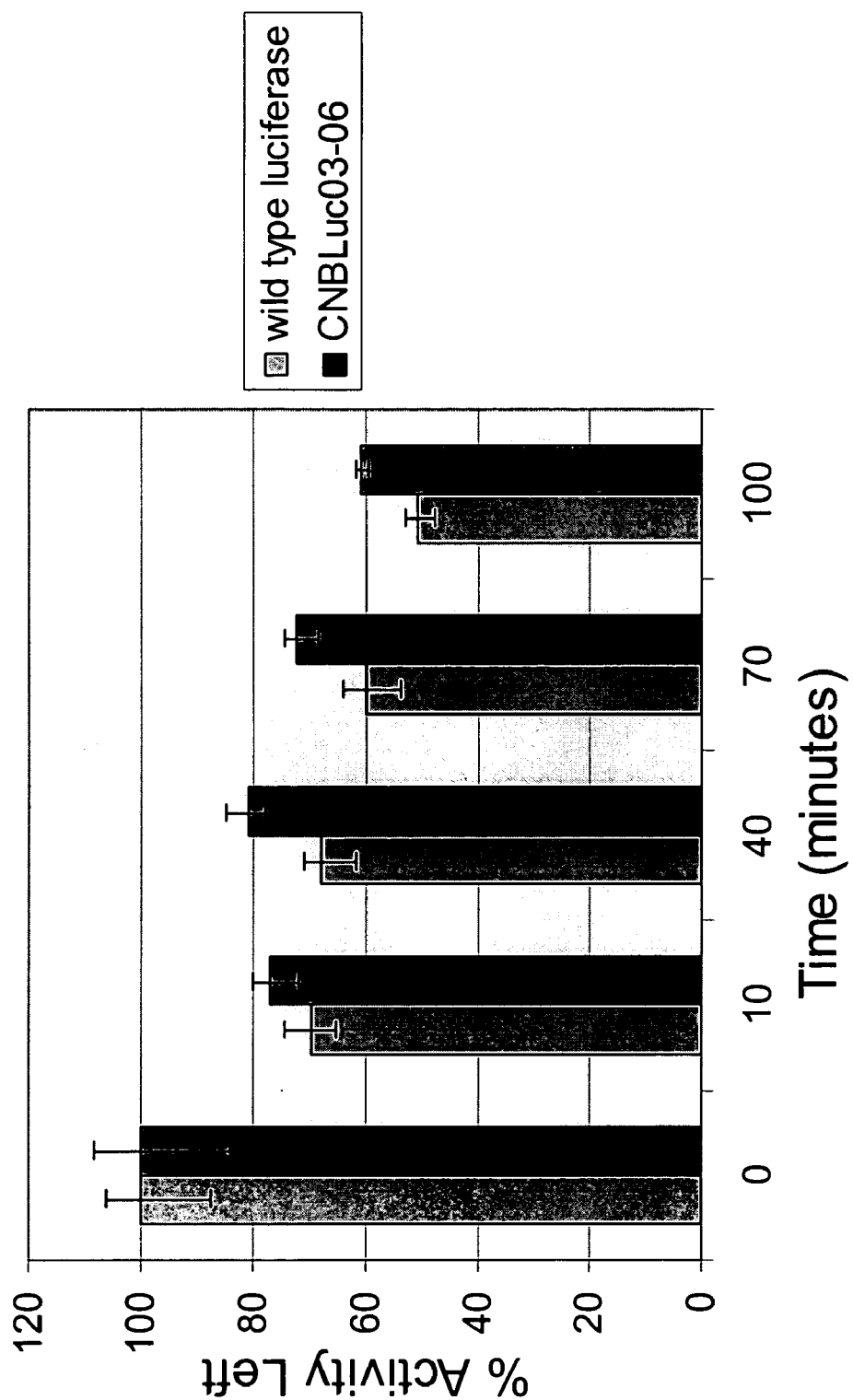
FIG. 7 is a plot comparing the activities of wild type luciferase and CNBLuc03-06 luciferase (SEQ ID NO: 4) kept at a temperature of 25° C. over time.
Figure 8:
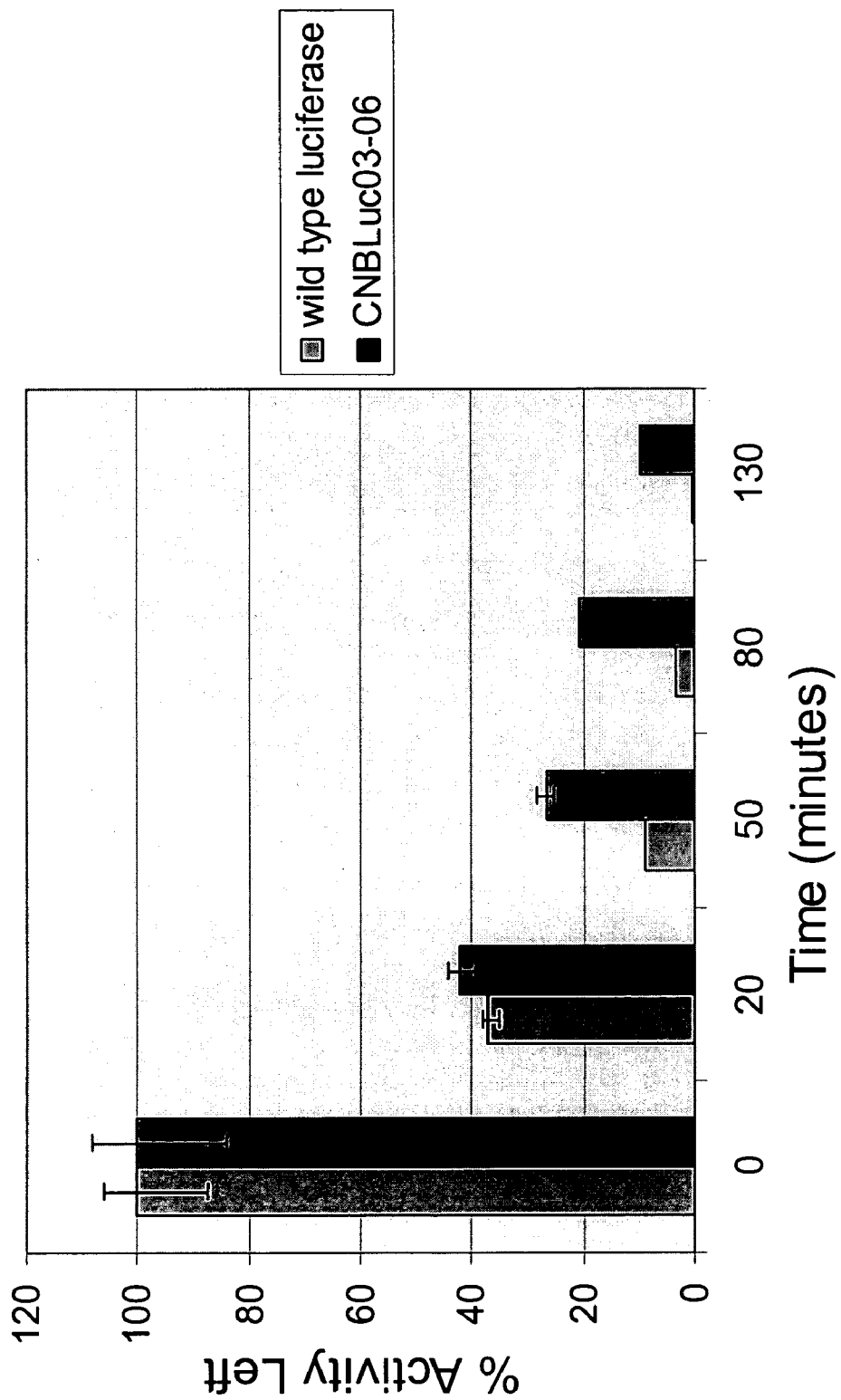
FIG. 8 is a plot comparing the activities of wild type luciferase and CNBLuc03-06 luciferase (SEQ ID NO: 4) kept at a temperature of 37° C. over time.

Both purified wild type luciferase and CNBLuc03-06 luciferase (SEQ ID NO: 4) were diluted to 10 µg/ml and aliquoted in three micro-centrifuge tubes for these storage stability studies conducted at different temperatures. The tubes containing wild type luciferase and CNBluc03-06 luciferase (SEQ ID NO: 4) were incubated at three different temperatures, 0° C. (FIG. 6), 25° C. (FIG. 7), and 37° C. (FIG. 8) over time. The assay contained 40 mM Tris-Acetate at pH 7.8, 1 mM $MgSO_4$, 0.1 mM EDTA, 500 µM D-Luciferin, 1 mM ATP, 0% ethanol and 33 mM DTT. The light output was measured every 30 minutes after two initial measurements at time 0 and 10 minutes. For each measurement all the samples were diluted to 2 µg/ml so that 10 µl of each sample could be added to give 20 ng of purified enzyme in each reaction.

At all three temperatures (0° C., 25° C., and 37° C.) CNBLuc03-06 luciferase (SEQ ID NO: 4) retained more activity than wild type luciferase. This shows that CNBLuc03-06 luciferase (SEQ ID NO: 4) has improved enzymatic properties of wild type luciferase in many aspects and is more stable than wild type luciferase to general denaturation.

EXAMPLE 5 pH Shift of CNBLuc03-06 Luciferase

CNBLuc03-06 luciferase (SEQ ID NO: 4) exhibits high activity at elevated pH (up to pH 11) under conditions which completely inhibit wild type luciferase. These improved enzyme characteristics can lead to a wider range of applications for in-vitro cytotoxicity screening in drug discovery and devleopment and toxicity testing of high production volume chemicals.

Figure 9:
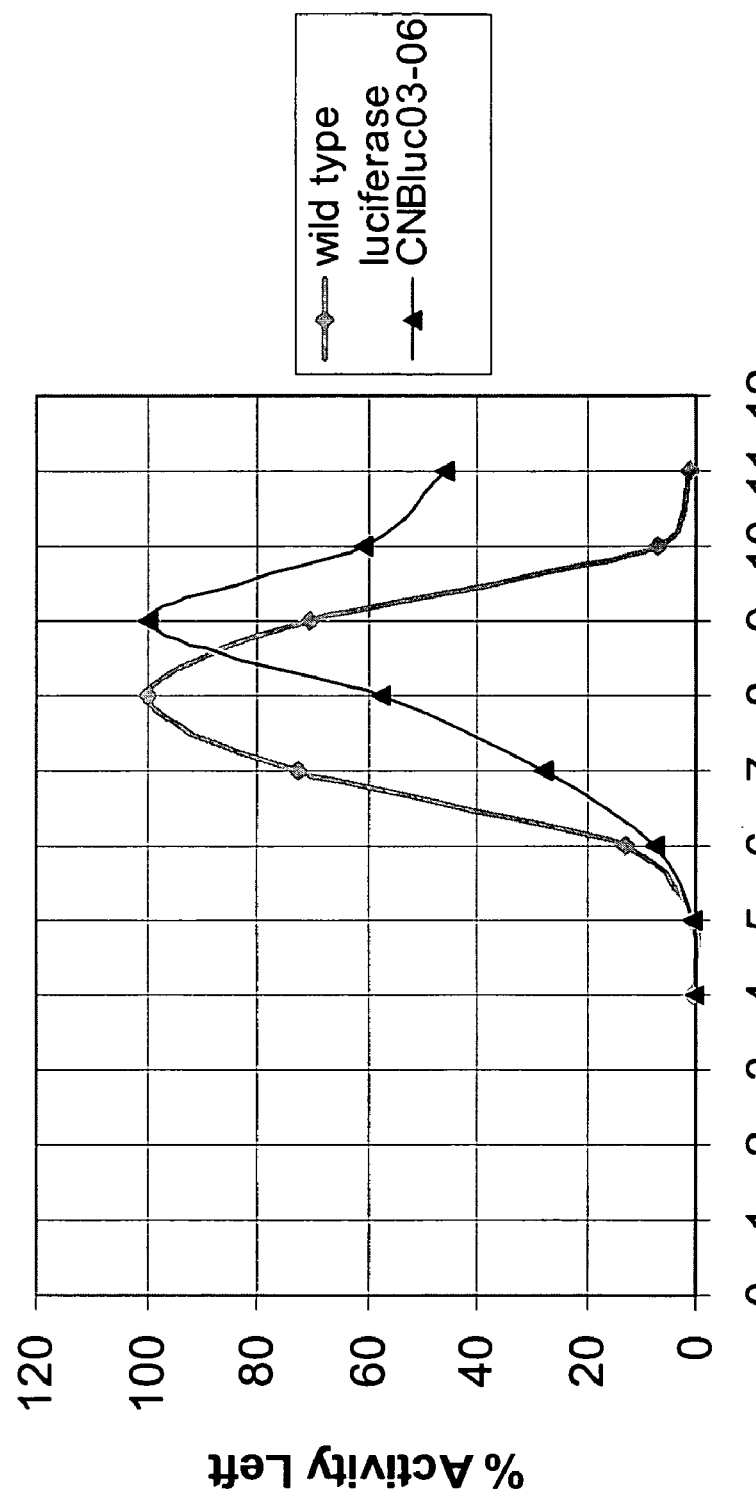
FIG. 9 plots wild type luciferase and CNBLuc03-06 luciferase (SEQ ID NO: 4) activity at different pHs.

FIG. 9 demonstrates the difference in optimum pH for wild type luciferase and CNBLuc03-06 luciferase (SEQ ID NO: 4). 20 ng of enzyme was used for each reaction. The pH was maintained at 7.8 by 40 mM Tris-acetate buffer and 33 mM DTT was added to each reaction. Both substrates, MGATP and D-Luciferin were saturated at 1 mM and 500 µM respectively. The values were normalized against the highest RLU (relative light units) at each pH optimum for comparison purpose. CNBLuc03-06 luciferase (SEQ ID NO: 4) has optimum pH of 9, but the high enough activity is retained at lower pHs in which enables us to use this mutant luciferase in case a wide range of pH is required for the assay (between 8–11).

EXAMPLE 6

DTT Effect of CNBLuc03-06 Luciferase

Dithiothreitol (DTT) is an enzyme stabilizing agent used to reduce disulfide bonds (break the bonds) that are not normally formed under physiological conditions. Both purified wild type luciferase and CNBLuc03-06 luciferase (SEQ ID NO: 4) were diluted to 2 µg/ml in 40 mM Tris Acetate buffer at pH 7.8. The assay contained 40 mM Tris-Acetate at pH 7.8, 1 mM MgSO4, 0.1 mM EDTA, 500 µM D-Luciferin, 1 mM ATP, and 0 mM DTT. The light output was measured over time and three replicate measurements were made for each luciferase. The average value of the highest light output reading obtained over time was used to determine specific activity of each enzyme.

CNBLuc03-06 luciferase (SEQ ID NO: 4) exhibited much higher activity ($9.6\pm0.4\times10^9$ RLU/mg enzyme/sec) compared to wild type luciferase ($2.9\pm1.6\times10^9$ RLU/mg enzyme/sec). These results show that CNBLuc03-06 luciferase (SEQ ID NO: 4) has improved activity in applications when DTT would interfere in assay performance, and may be of benefit in applications when luciferase is carried into cells with a passport protein in gene reporter assays.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation lawfully accorded the appended claims.

All patents, publications and references cited herein are hereby fully incorporated by reference. In case of conflict between the present disclosure and incorporated patents, publications and references, the present disclosure should control.

---

The invention claimed is:

1. A modified luciferase which exhibits greater activity in the presence of chloroform than wild type luciferase of SEQ ID NO: 6 in the presence of chloroform, comprising a polypeptide having an amino acid sequence which differs from SEQ ID NO: 6 in that serine is replaced by threonine at amino acid 239.

2. A modified luciferase which exhibits greater activity in the presence of chloroform than wild type luciferase of SEQ ID NO: 6 in the presence of chloroform, comprising a polypeptide which differs from SEQ ID NO: 6 in that serine is replaced by threonine at amino acid 239 and alanine is replaced by threonine at amino acid number 532.

3. A modified luciferase which exhibits greater activity in the presence of chloroform than wild type luciferase of SEQ ID NO: 6 in the presence of chloroform, comprising a polypeptide which differs from SEQ ID NO: 6 in that serine is replaced by threonine at amino acid 239, alanine is replaced by threonine at amino acid number 532 and aspartic acid is replaced by tyrosine at amino acid 357.

4. A modified luciferase which exhibits greater activity in the presence of chloroform than wild type luciferase (SEQ ID NO: 6) in the presence of chloroform, comprising a polypeptide having an amino acid sequence which differs from SEQ ID NO: 6 in that alanine is replaced by threonine at amino acid number 532.

5. A polypeptide comprising an amino acid sequence selected from the group consisting of SEQ ID NO: 2 and SEQ ID NO: 4.

6. The polypeptide of claim 5 wherein the amino acid sequence is SEQ ID NO: 2.

7. The polypeptide of claim 5 wherein the amino acid sequence is SEQ ID NO: 4.

8. A fusion protein comprising the polypeptide of claim 5.

9. A polynucleotide encoding the polypeptide of claim 5.

10. The polynucleotide of claim 9 wherein the amino acid sequence is SEQ ID NO: 2.

11. The polynucleotide of claim 10 wherein the polynucleotide is SEQ ID NO: 1.

12. The polynucleotide of claim 9 wherein the amino acid sequence is SEQ ID NO: 4.

13. The polynucleotide of claim 12 wherein the polynucleotide is SEQ ID NO: 3.

14. A vector comprising the polynucleotide of claim 9.

15. A host cell comprising the vector of claim 14.

* * * * *